United States Patent [19]

Hiltebrandt

[11] Patent Number: 4,807,595
[45] Date of Patent: Feb. 28, 1989

[54] SALPINGOSCOPE

[75] Inventor: Siegfried Hiltebrandt, Knittlingen, Fed. Rep. of Germany

[73] Assignee: Richard Wolf GmbH, Fed. Rep. of Germany

[21] Appl. No.: 62,697

[22] Filed: Jun. 16, 1987

[30] Foreign Application Priority Data

Dec. 30, 1986 [DE] Fed. Rep. of Germany ....... 3644728

[51] Int. Cl.$^4$ .............................................. A61B 1/00
[52] U.S. Cl. ...................................................... 128/4
[58] Field of Search ........................... 128/4, 5, 6, 7, 3

[56] References Cited

U.S. PATENT DOCUMENTS

| 1,880,551 | 10/1932 | Wappler | 128/7 |
| 3,261,350 | 7/1966 | Wallace | 128/6 |
| 4,103,680 | 8/1978 | Yoon | 128/6 |
| 4,567,880 | 2/1986 | Goodman | 128/7 |

Primary Examiner—William H. Grieb
Attorney, Agent, or Firm—Hill, Van Santen, Steadman & Simpson

[57] ABSTRACT

For the examination of the fallopian tube, a salpingoscope has a first endoscope telescopically receiving a second endoscope which are displaceable relative one another. The optics of the second endoscope and the distal end of the outer guide shaft of the second endoscope are matched to the small diameter of the fallopian tube. An inner shaft guarantees an adequate stability of the thin optics of the second endoscope and an obturator may be used to replace the optics of the second endoscope while introducing the constricted end section of the outer shaft into the fallopian tube.

10 Claims, 2 Drawing Sheets

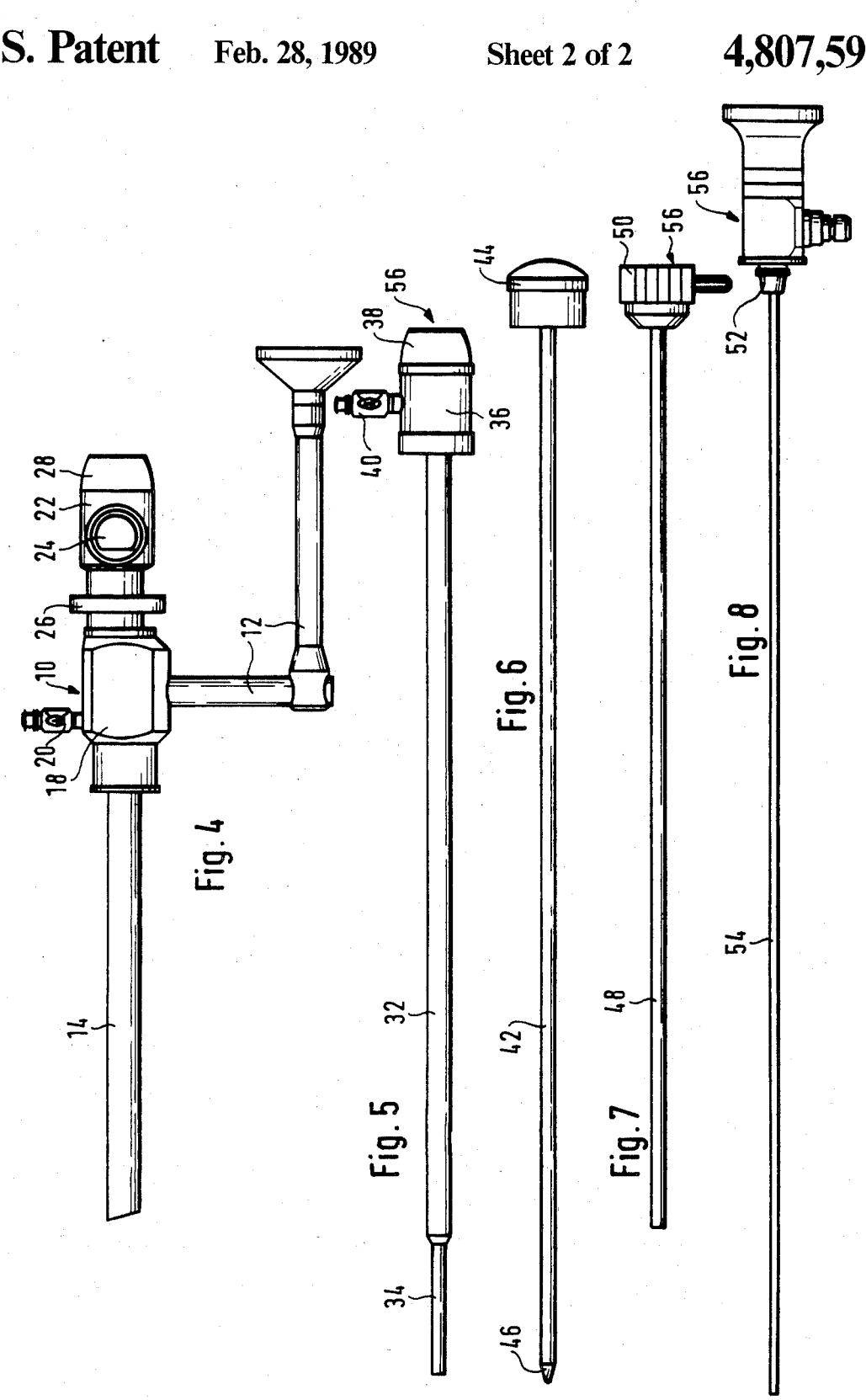

SALPINGOSCOPE

BACKGROUND OF THE INVENTION

The present invention is directed to a salpingoscope for the examination of fallopian tubes. The salpingoscope includes a first endoscope, that has an angular optical part and an instrument channel, and a second endoscope, which includes an outer shaft which is slidably received in the instrument channel of the first endoscope with the outer shaft containing the optics for the second endoscope. The examination of the fallopian tubes includes positioning the first endoscope with its distal end adjacent the fallopian tube, then inserting the shaft of the second endoscope through the instrument channel of the first endoscope with the distal end of the second endoscope being inserted into the fallopian tube.

Infertility, for example, the incapacity of carrying a pregnancy full term to a viable child, can be attributed to, among other things, functional or anatomical causes, such as, for example, concrescences of the fallopian tube or to an intramural tube closure, for example, to a myoma situated in the wall of the fallopian tube. When other causes of an existing infertility are to be excluded on the basis of appropriate examination which has already been carried out, it is then necessary to examine both the perviousness of the fallopian tube as well as the mucosa of the fallopian tube for potential irregularities.

A known surgical laparoscope is usually employed for this purpose. The laparoscope comprises a first endoscope having an angled ocular part as well as an instrument channel for the introduction of surgical instruments. A second, thinner endoscope, which serves the purpose of observing the fallopian tube, is introduced through the instrument channel instead of the surgical instrument. An outside shaft is coupled to the second endoscope at the proximal side and sometimes serves the purpose of stiffening the second endoscope. This outside shaft is, likewise, co-introduced into the instrument channel. As soon as the distal end of the second endoscope is introduced into the fallopian tube, the fallopian tube must be fixed in a sealed fashion to the shaft of the second endoscope by forceps inserted through a second incision so that the fallopian tube can be subsequently dilated with a wash. As a result of this fixing of the shaft, no further displacement of the second endoscope optics within the fallopian tube is now possible. Due to their shape, moreover, the shafts of the known endoscopes are very difficult to introduce into the fallopian tube.

SUMMARY OF THE INVENTION

The object of the present invention is to create a salpingoscope, with which a complete and easily executed examination with direct viewing is possible over the entire length of the fallopian tube.

To accomplish this object, the present invention is directed to an improved method of an examination using an improved salpingoscope. The salpingoscope has a first endoscope that has an angular ocular part and an instrument channel in which a second endoscope comprising an outer shaft is displaceable in a longitudinal direction of the first endoscope. The improvements in this salpingoscope are that the second endoscope comprises an outer shaft, which has its distal end projecting beyond the instrument channel of the first endoscope and also includes an inner shaft immediately surrounding the optics of the second endoscope, the distal end section or portion of the outer shaft comprises a part having a reduced diameter which will extend up to the end and from which the optics of the second endoscope will project and in which the latter is displaceable in a guided fashion. With the improved salpingoscope, the method has the improvement that the reduced diameter distal end portion of the shaft of the second endoscope is inserted into the fallopian tube and then the optics of the second endoscope are freely displaceable along the full direction of the tube for observation.

By constricting the outer shaft and its end section projecting fom the instrument channel, an extremely thin shaft part can be comfortably introduced into the fallopian tube together with the distal end of the optics. The fallopian tube can then be fixed to the shaft by a known means, whereupon the distal end of the optics can still be displaced over the entire length of the fallopian tube with respect to the outer shaft. The inner shaft increases the mechanical stability of the thin optics in order to avoid damage to the optical system.

German Utility Model No. 78 33 379 already discloses an endoscope arrangement comprising two endoscopes axially displaceable relative to one another. However, this arrangement is not suitable for introduction into a fallopian tube due to the disadvantages as initially cited with regard to the prior art devices.

German Patent No. 1,964,603 discloses a flexible endoscope which, likewise, comprises a channel for the introduction of a second endoscope. In view of the examination of fallopian tubes, this known arrangement has the same disadvantages as the abovementioned prior art.

So that no injuries can occur, given the introduction of the distal end section of the second endoscope shaft as it is inserted into the fallopian tube, an obturator is inserted in the shaft of the second endoscope with its rounded end projecting beyond the end of the shaft. After the step of introducing the reduced distal end portion of the second shaft has been accomplished, the obturator is then removed and the optics of the second endoscope are then inserted.

A trumpet valve or slide valve arrangement is preferably provided on the instrument channel so that the instrument channel can be tightly closed during the introduction and interchange of various parts.

Suitable seals and coupling parts are expediently provided for gas-tight and liquid-tight sealing and for mutual connecting of the parts together.

In another advantageous development of the invention, the dilation fluid for the fallopian tube can be supplied and discharged through a thin annular channel between the constricted part of the outer shaft and the optics of the second endoscope.

The measures of the invention are also preferably employed in a surgical laparoscope used as a first endoscope in whose instrument channel the inventively fashioned second endoscope has been arranged.

Other advantages and features of the invention will be readily apparent from the following description, drawings and claims.

BRIEF DESCRIPTION OF THE DRAWINGS

FIG. 4 is a side view of the first endoscope in accordance with the present invention;

FIG. 5 is a side view of an outer shaft with the connecting housing of the second endoscope in accordance with the present invention;

FIG. 6 is a side view of an obturator introducable into the outer shaft;

FIG. 7 is a side view of an inner shaft with a connecting part of the second endoscope in accordance with the present invention; and FIG. 8 is a side view of the optics of the second endoscope with a connecting part and ocular.

DESCRIPTION OF THE PREFERRED EMBODIMENT

Figure 1:
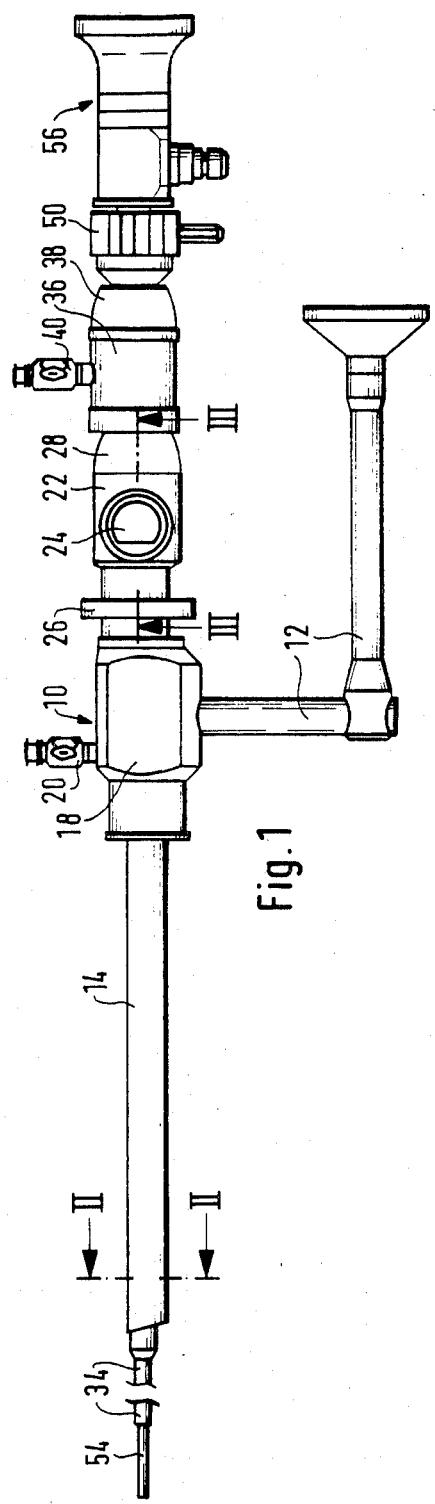
FIG. 1 is a side view of a salpingoscope in accordance with the present invention.

The principles of the present invention are particularly useful in a salpingoscope which is composed of a first endoscope 10 and a second endoscope 56, as illustrated in FIG. 1.

As best illustrated in FIG. 4, the first endoscope 10 has an angular ocular part 12 and a rigid instrument shaft 14. The optical system, not shown in great detail, is arranged in the ocular part 12 and continues through a connecting part 18 and within the instrument shaft 14 up to the distal end, as may be seen by the optical guide 16 of FIG. 2.

The connector part 18 (FIG. 4) has a closable connecting or valve cock 20 and is interconnected to a set-up part or housing 22 by a coupling part 26. The housing 22, on its proximal end, is provided with a sealing cap 28 and includes a slide valve or trumpet valve 24. The valve 24 has a slidable member urged from an open position, which is illustrated in FIG. 3, to a closed position by a spring.

Figure 3:
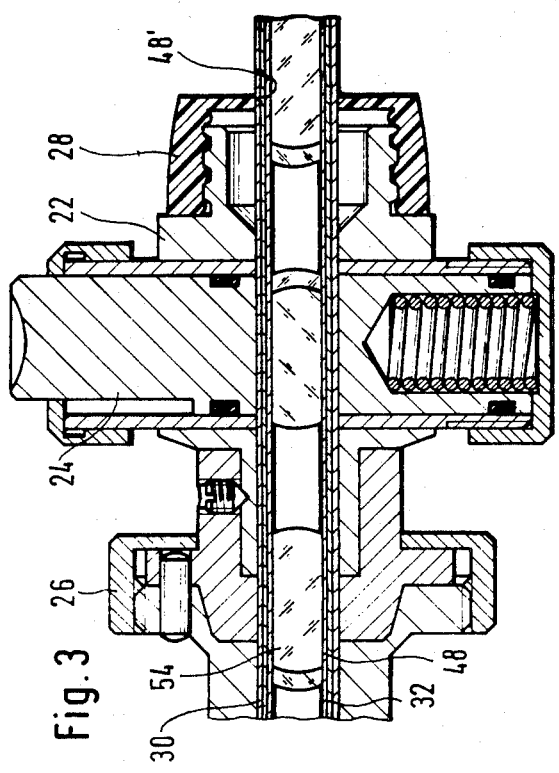
FIG. 3 is an enlarged partial cross sectional view taken along the lines III—III of FIG. 1.
Figure 2:
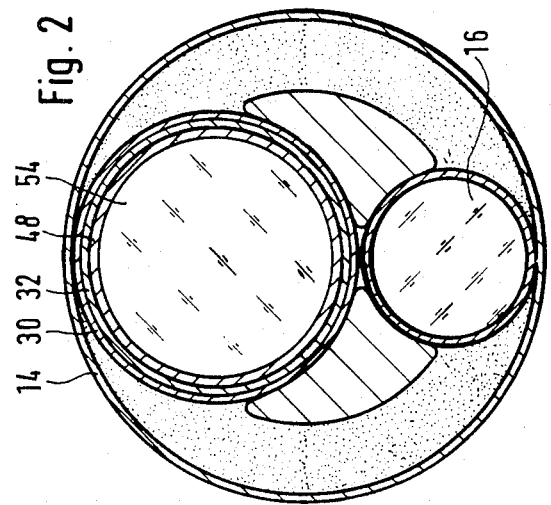
FIG. 2 is an enlarged cross sectional view taken along lines II—II of FIG. 1.

The instrument shaft 14, the connector part 18 and the housing 22 are penetrated by an instrument channel 30, which is best illustrated in FIGS. 2 and 3. The instrument channel 30 is in communication with the connecting cock 20 in a way not shown in great detail.

The second endoscope 56 includes an outer shaft 32 (FIG. 5), which is introduced into the instrument channel in a guiding fashion preceding from the proximal end of the first endoscope 10. The shaft 32, at its distal end, has a first end part or section 34, which has a smaller or constricted diameter and, as illustrated in FIG. 1, will project from the distal end of the instrument shaft 14 of the first endoscope 10. The shaft 32, at its proximal end, has a connector part 36 which, as illustrated in FIG. 1, presses against the sealing cap 28 of the part 22 and this connector part 36, likewise, is provided with a sealing cap 38 and with a closable connecting or valve cock 40, which is in communication with the interior of the shaft 32.

In operation, the end part 34 of section 32 is introduced into the fallopian tube. During this step, to prevent injury by the distal edge of the part 32, an obturator 42 (FIG. 6), which has a head 44 at its proximal end and has a rounded distal end 46 is inserted into the interior of the shaft 32 with the rounded distal end 46 projecting out of the distal end of the end part or section 34. This rounded end 46 will reduce injuries by the distal edge of the end section or part 34. After the introduction of the end part 34 into the fallopian tube and a securing or sealing therein, the obturator 42 is withdrawn from the outer shaft 32 and an inner shaft 48 (FIG. 7), whose outside diameters and inside diameters roughly correspond to the diameters of the end section 34 is then introduced into the nonconstricted or reduced diameter portion of the outer shaft 32. The shaft 48 has a coupling part 50 at its proximal end, which part 50 coacts with a coupling part 52 of the optics 54 to interconnect the optics in the inner shaft 48. The second endoscope 56 thus, primarily, consists of the outer shaft 32, the inner shaft 48 and the optics 54, which are all telescoped within one another. The length of the optics 54 is selected so that its distal end will project beyond the end part 34, as illustrated in FIG. 1, when the second endoscope 56 is completely inserted into the first endoscope 10. By axial displacement of the optics 54, the entire length or desired portion of the fallopian tube can be visually examined.

The sealing caps 28 and 38 are composed of elastic material. As illustrated in FIG. 3, the cap 28 has an axial opening 48' which will press against the outside of a tube inserted into the instrument channel 30 in an elastically sealing fashion and with a non-positive lock up to a certain degree. A gas-tight and liquid-tight closure between the outside atmosphere and the inside of the instrument is thus attained and, thus, also a sealing of the examined body cavity. The sealing cap 38 is substantially the same as the cap 28 and has an opening which will engage either the outside of the obturator 42 or the inner shaft 48 in a sealing manner. Thus, non-positive connections between the sealing cap 28 and the shaft 32, as well as the sealing cap 38 and the shaft 48, will be obtained and can be overcome by exerting an axial pull or pressure therebetween.

The inside diameter of this constricted end part or section 34 of the outer shaft 32 is slightly larger than the outside diameter of the optics 54 of the second endoscope 56. Thus, a thin, annular channel will be formed between the inner surface of the constricted part 34 and the outer surface of the optics 54 and this channel can be used to supply and remove a wash fluid which is introduced by the valve cock 40.

The diameter of the optics 54 of the second endoscope is matched to the small diameter of the fallopian tube to be examined. In order to at least partially compensate for the low stability of the optics 54, it is surrounded by the inner shaft 48 within the wider section of the outer shaft 32 and is subsequently guided through the constricted end section or part 34 of the outer shaft. The diameter of the constricted end part or section 34 is, likewise, still so small that it can be easily introduced into the fallopian tube to a depth of 10–20 mm and the fallopian tubes can then be sealed to the end section 34 in a known manner by means of forceps or the like. After supplying a dilation fluid through the cock 40 and the annular channel which extends between the end section 34 and the optics 54, a visual examination of the fallopian tube can be obtained by axial displacement of the optics 54 relative to the outer shaft 32 and the end section 34.

Although various minor modifications may be suggested by those versed in the art, it should be understood that I wish to embody within the scope of the patent granted hereon all such modifications as reasonably and properly come within the scope of my contribution to the art.

I claim:

1. In a method for the examination of the fallopian tube in which a first endoscope is positioned with its distal end adjacent to the fallopian tubes from the outside and a second, thinner endoscope is supported in a guided fashion in the first endoscope and has its distal end introduced into the fallopian tube, the improvements comprising providing a second endoscope having a shaft surrounding the optics, said shaft having a distal end of a reduced diameter, said step of introducing the second endoscope includes inserting the distal end of a reduced diameter into the fallopian tube and then positioning the optics of the second endoscope to project from the distal end and to be freely displaced in a longitudinal direction of the shaft of the second endoscope and the fallopian tube.

2. In a method according to claim 1, wherein, prior to the step of inserting the distal end of a reduced diameter into the fallopian tube, replacing the optics of the second endoscope with an obturator so that during insertion of the distal end damage to the tube by the distal edge is substantially eliminated and then, subsequent to the step of inserting, removing the obturator and replacing it with the optics of the second endoscope.

3. In a salpingoscope for the examination of the fallopian tube, said salpingoscope including a first endoscope that has an angular ocular part and an instrument channel through which a second endoscope comprising an outer shaft is displaceable in a longitudinal direction of the first endoscope, the improvements comprising said second endoscope comprising an outer shaft which has a distal end section projecting beyond the instrument channel of the first endoscope, an inner shaft immediately surrounding an optics of the second endoscope, the distal end section of said outer shaft comprising a portion having a reduced diameter which extends up to the end thereof and the optics of the second endoscope projecting out of the end of the reduced diameter portion of the outer shaft and being displaceable in a guided fashion therein.

4. In a salpingoscope according to claim 3, wherein said inner shaft has a length so that the distal end portion terminates adjacent to a point of merging of the end portion and remaining portion of the outer shaft and wherein the diameters of said end section of the outer shaft is approximately the same as the diameters of the inner shaft.

5. In a salpingoscope according to claim 3, wherein the optics of the second endoscope, together with the inner shaft, are interchangeable with an obturator which has a rounded end for projecting from the distal end of said outer shaft.

6. In a salpingoscope according to claim 3, wherein the first endoscope has a slide valve for closing the instrument channel when the second endoscope is removed therefrom.

7. In a salpingoscope according to claim 3, wherein the first endoscope has a seal cap adjacent its proximal end and the second endoscope has a seal cap adjacent the proximal end of the outer shaft, said seal caps each having an opening for receiving a tube and forming a gas-tight and liquid-tight seal therewith.

8. In a salpingoscope according to claim 7, wherein a proximal end of the inner shaft has a coupling part coacting with a coupling part on the proximal end of the optics of the second endoscope for coupling the inner shaft and optics together.

9. In a salpingoscope according to claim 3, wherein the outer diameter of the optics and the inner diameter of the end section of the outer shaft are selected relative to one another to form a thin annular channel for introducing and removing wash fluids.

10. In a salpingoscope according to claim 3, wherein the first endoscope is a surgical laparoscope which has the instrument channel which receives the second endoscope.

* * * * *